US00PP37507P2

(12) United States Plant Patent
Nannes

(10) Patent No.: US PP37,507 P2
(45) Date of Patent: Jun. 30, 2026

(54) ***SAXIFRAGA* PLANT NAMED 'BINL-110925'**

(50) Latin Name: *Saxifraga stolonifera*
Varietal Denomination: BINL-110925

(71) Applicant: Botanical Innovation B.V., Wageningen (NL)

(72) Inventor: Jacobus A. M. Nannes, Nairobi (KE)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 19/344,963

(22) Filed: Sep. 30, 2025

(51) Int. Cl.
*A01H 5/12* (2018.01)
*A01H 6/80* (2018.01)

(52) U.S. Cl.
USPC ..... Plt./263.1

(58) Field of Classification Search
USPC ..... Plt./263.1
See application file for complete search history.

*Primary Examiner* — Susan Mccormick Ewoldt

(57) ABSTRACT

A new and distinct cultivar of *Saxifraga* plant named 'BINL-110925' is disclosed, characterized by distinctly variegated leaves with a unique combination of colors. Variegated leaves have a green center, an irregular white leaf margin, and grey-green veins that sometimes widen into bigger grey-green spots. Young foliage has a Greyed-Red petiole. The new variety is a *Saxifraga*, typically produced as a garden or container plant.

2 Drawing Sheets

Latin name of the genus and species: *Saxifraga stolonifera.*

Variety denomination: 'BINL-110925'.

BACKGROUND OF THE INVENTION

The new cultivar is a product of a naturally-occurring branch mutation. The parent cultivar is the unpatented *Saxifraga stolonifera* 'Tricolor'. The new cultivar was found and selected by the inventor in August 2022 at a nursery in Nairobi, Kenya.

Asexual reproduction of the new cultivar 'BINL-110925' was first performed in Nairobi, Kenya in May 2023, by vegetative cuttings made from runners. 'BINL-110925' has since produced several generations and has shown that the unique features of this cultivar are stable and reproduced true to type.

SUMMARY OF THE INVENTION

The cultivar 'BINL-110925' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-110925'. These characteristics in combination distinguish 'BINL-110925' as a new and distinct *Saxifraga* cultivar:

1. Distinctively variegated leaves with a unique combination of colors. Variegated leaves have a green center, an irregular white leaf margin and grey-green veins that sometimes widen into bigger grey-green spots.

PARENTAL COMPARISON

Plants of the new cultivar 'BINL-110925' are similar to the parent in most horticultural characteristics. However, plants of the new variety differ in the following:

1. Leaves of the new variety are variegated with a green center, an irregular white leaf margin, and grey-green veins that sometimes widen into bigger grey-green spots. Leaves of the parent are variegated with a green center, an irregular pinkish-white leaf margin, and fine grey-green veins.

COMMERCIAL COMPARISONS

'BINL-110925' can be compared to the commercial variety *Saxifraga stolonifera* 'Dark Green', unpatented. The two varieties are similar in most horticultural characteristics; however, the new variety differs in the following:

1. Leaves of the new variety are variegated with a green center, an irregular white leaf margin, and grey-green veins that sometimes widen into bigger grey-green spots. Leaves of this comparator are non-variegated, having a dark green color with a fine grey-green vein.

'BINL-110925' can be compared to the unpatented commercial variety *Saxifraga stolonifera*, the species itself. The two plants are similar in most horticultural characteristics; however, the new variety differs in the following:

1. Leaves of the new variety are variegated with a green center, an irregular white leaf margin, and grey-green veins that sometimes widen into bigger grey-green spots. Leaves of this comparator are non-variegated, having a dark green color with a grey-green veins.

BRIEF DESCRIPTION OF THE PHOTOGRAPHS

Figure 1:
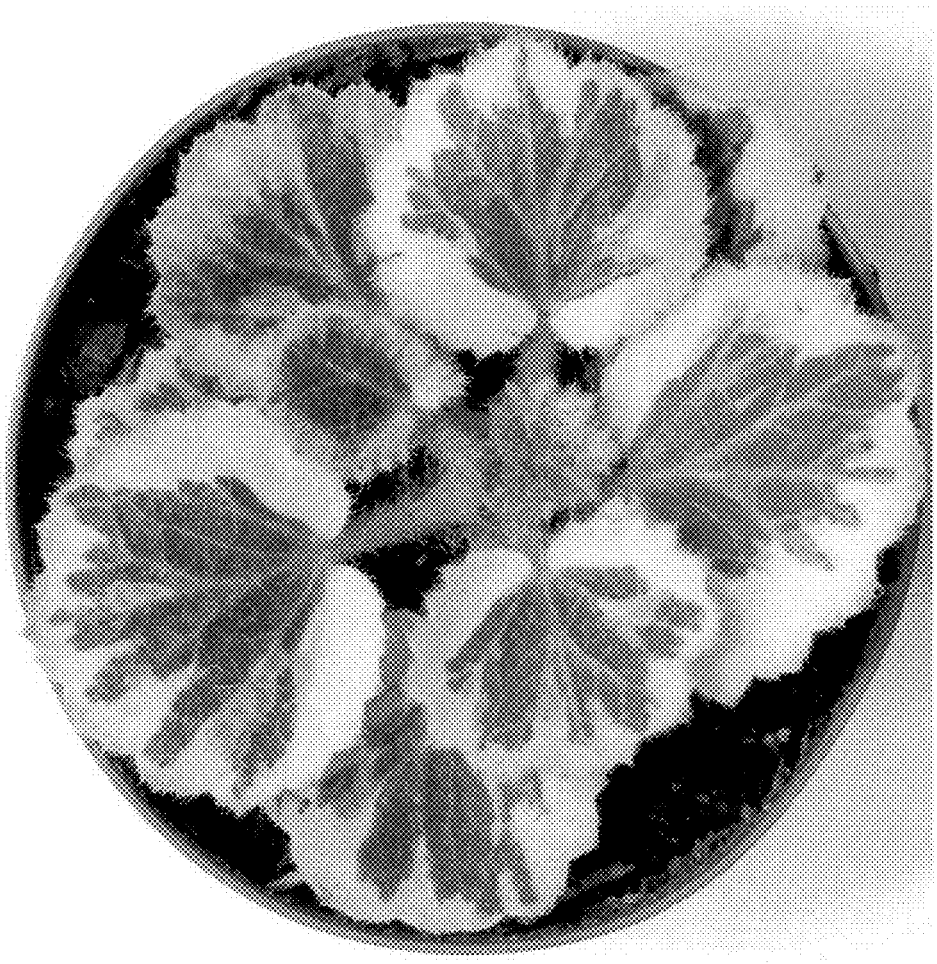

The accompanying photograph in FIG. 1 illustrates in full color a typical plant of 'BINL-110925' grown in a greenhouse in Nairobi, Kenya. This plant is approximately 10 weeks old, shown in a 15 cm container.

Figure 2:
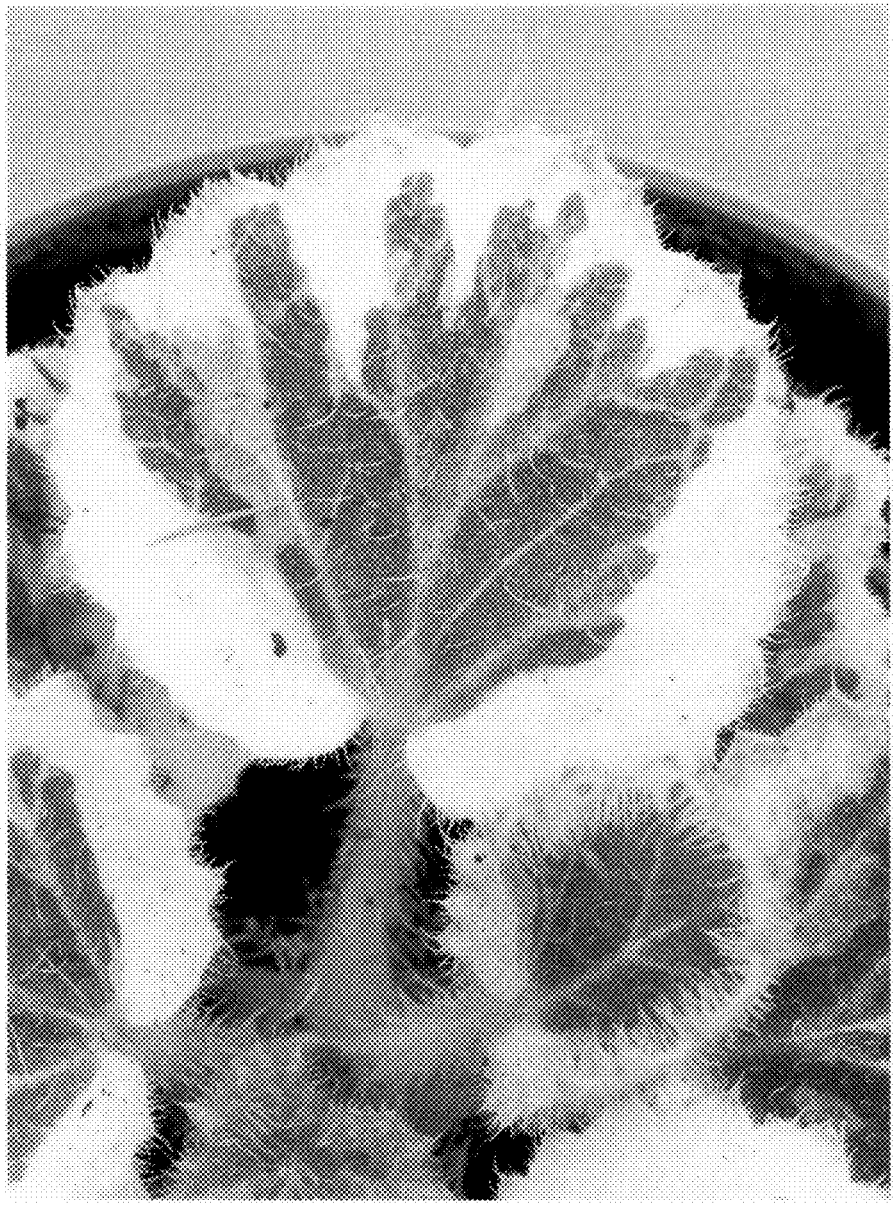

FIG. 2 illustrates a close up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'BINL-110925' plants in a glass greenhouse in Nairobi, Kenya. Temperatures ranged from 20° C. to 28° C. during the day, and 12° C. to 20° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Saxifraga stolonifera* 'BINL-110925'.

PROPAGATION

Time to initiate roots: 7 days in summer; 14 days in winter at 20° C.

Time to produce rooted cutting: 30 days in summer; 45 days in winter at 20° C.

Root description: Thin, herbaceous, moderately dense and freely-branching. White in color, not accurately measured with The R.H.S. Chart.

Propagation method: Terminal vegetative cuttings.

PLANT

Plant type: Perennial.

Age of the plant described: 10 weeks.

Growth habit: Mounding, then trailing.

Container size: 7 cm pots and larger.

Height: Average 4.4 cm to the top of foliage; no flowering observed.

Plant spread: Average 8.2 cm.

Branching characteristics: Leaves in basal rosettes, no main stems or lateral stems present on a plant of 10 weeks.

FOLIAGE

Leaf:

*Arrangement*.—Single rosette.

*Quantity*.—Average 11 leaves per rosette.

*Average length*.—3.7 cm.

*Average width*.—4.1 cm.

*Whole leaf shape*.—Reniform to near orbicular.

*Whole leaf aspect and angle of attachment*.—Flat, petioles in an average angle of 40° to horizontal.

*Apex*.—Minutely abruptly acute.

*Base*.—Cordate to reniform.

*Margin*.—Dentate.

*Texture of top surface*.—Smooth, densely pubescent.

*Texture of bottom surface*.—Smooth, densely pubescent.

*Pubescence*.—Both sides densely pubescent with short strigose hairs, on upper side, average length: 0.2 cm, colored transparent RHS White N155A, on under side, average length: 0.1 cm, colored Greyed-Red 182C.

*Rugosity*.—Both sides non-rugose.

*Luster*.—Upper side: Matte to very slightly glossy. Under side: Slightly glossy.

*Color*.—Young foliage upper side: RHS Yellow-Green 141A; irregularly margined Yellow-Green 151A and 152D, narrowly edged Greyed-Red 182A and 182B, petiole Greyed-Green 195A and 195B, densely pubescent with short strigose hairs, average length: 0.2 cm, colored transparent Greyed-Red 182A. Young foliage under side: RHS Yellow-Green 148D, irregularly margined Yellow-Green 151D, narrowly edged Greyed-Red 182B, petiole Yellow-Green 146C, densely pubescent with short strigose hairs, average length: 0.2 cm, colored transparent Greyed-Red 182A. Mature foliage upper side: RHS Green NN137C, broadly irregularly margined Yellow-Green 150D and a blend of 145D and near 150D, leaf narrowly edged (tips of teeth) Yellow-Green 144A and 144B. Mature foliage under side: RHS Yellow-Green; 147C, broadly irregularly margined 145C, leaf narrowly edged (tips of teeth) 145A.

*Venation*.—Pattern: Laciniate. Color, upper side: RHS Greyed-Green 191A and 191B. Color, under side: RHS Yellow-Green N148C.

Petioles:

*Length*.—Average: 2.2 cm

*Diameter*.—Slightly flattened, average width (horizontal) 0.3 cm.

*Height* (*vertical*).—Average 0.25 cm.

*Texture*.—Smooth, densely pubescent with short somewhat adpressed, strigose hairs, on both sides average length: 0.2 cm, on upper side colored transparent near RHS Greyed-Orange N170D and lighter, on under side colored near Greyed-Red 182D.

*Luster*.—Slightly glossy.

*Strength*.—Medium.

*Color, upper side*.—RHS Yellow-Green N148A.

*Color, under side*.—RHS Yellow-Green 146D.

Stipules:

*Average length*.—0.5 cm.

*Average width*.—0.2 cm.

*Margin*.—Densely pubescent with short strigose hairs, average length: 0.2 cm, colored near transparent RHS Greyed-Orange N170D, both sides of stipules colored Yellow-Green 144C.

FLOWER

Flowering not observed to date.

REPRODUCTIVE ORGANS

Not observed to date.

OTHER CHARACTERISTICS

Seeds and fruits: Not observed to date.

Temperature tolerance: Typically USDA zone 6 to 9.Observed to tolerate temperatures between 5° C. and 35° C.

Disease/pest resistance: Neither resistance nor susceptibility to normal diseases and pests of *Saxifraga* observed.

What is claimed is:

1. A new and distinct cultivar of *Saxifraga* plant named 'BINL-110925' as herein illustrated and described.

* * * * *